United States Patent
Sawada et al.

(10) Patent No.: US 7,049,645 B2
(45) Date of Patent: May 23, 2006

(54) FET TYPE SENSOR, ION DENSITY DETECTING METHOD COMPRISING THIS SENSOR, AND BASE SEQUENCE DETECTING METHOD

(75) Inventors: Kazuaki Sawada, Toyohashi (JP); Masakatsu Uchiyama, Kyoto (JP)

(73) Assignee: Bio-X Inc., Kyoto (JP)

( * ) Notice: Subject to any disclaimer, the term of this patent is extended or adjusted under 35 U.S.C. 154(b) by 0 days.

(21) Appl. No.: 10/495,808

(22) PCT Filed: Nov. 11, 2002

(86) PCT No.: PCT/JP02/11752

§ 371 (c)(1),
(2), (4) Date: Nov. 5, 2004

(87) PCT Pub. No.: WO03/042683

PCT Pub. Date: May 22, 2003

(65) Prior Publication Data

US 2005/0062093 A1    Mar. 24, 2005

(30) Foreign Application Priority Data

Nov. 16, 2001 (JP) .............................. 2001-351657

(51) Int. Cl.
*H01L 31/062* (2006.01)
*H01L 31/113* (2006.01)

(52) U.S. Cl. ...................................... 257/292; 257/291

(58) Field of Classification Search ................ 257/290, 257/291, 292
See application file for complete search history.

(56) References Cited

U.S. PATENT DOCUMENTS

| 4,156,818 A | * | 5/1979 | Collins et al. ................ 377/58 |
| 4,275,315 A | * | 6/1981 | Maeding et al. .............. 377/58 |
| 4,974,240 A | * | 11/1990 | Suzuki et al. ................. 377/60 |

FOREIGN PATENT DOCUMENTS

| JP | 60-247151 | 12/1985 |
| JP | 6-249826 | 9/1994 |
| JP | 8-278281 | 10/1996 |
| JP | 10-332423 | 12/1998 |
| JP | 2001-33274 | 2/2001 |
| JP | 2001-511245 | 8/2001 |
| JP | 2002-9274 | 1/2002 |
| JP | 2002-98667 | 4/2002 |

* cited by examiner

Primary Examiner—Ngân V. Ngô
(74) Attorney, Agent, or Firm—Hodgson Russ LLP

(57) ABSTRACT

The surface of a semiconductor substrate (1) comprises an input diode section (2) and a floating diffusion section (3) consisting of a diffusion region reverse to the substrate in conductivity type, an input gate (6) and an output gate (7) fixed on an insulation film (5) extending from an input diode section to a floating diffusion section, a sensing section (9) consisting of an ion sensitive film fixed on the insulation film extending from the input.

8 Claims, 10 Drawing Sheets

FET TYPE SENSOR, ION DENSITY DETECTING METHOD COMPRISING THIS SENSOR, AND BASE SEQUENCE DETECTING METHOD

This application is a 371 of PCT/JP02/11752 filed Nov. 11, 2002.

FIELD OF THE INVENTION

The present invention relates to a structure of FET type sensor for detecting ion density by forming a sensing section responding to ions on a gate insulation film of a MOS type field effect transistor (FET), and detecting changes of potential level of channel on the basis of the potential change of the surface of the sensing section, an ion density detecting method comprising this sensor structure, and a base sequence detecting method.

PRIOR ART

As chemical sensors making use of integrated circuit technology, so far, various sensors have been developed on the basis of the principle of FET. The FET type sensor is for detecting electrochemical potential changes, and, for example, an ion sensitive FET (ISFET) for detecting hydrogen ion density is known.

The ISFET forms a sensing section responding to ions on a gate insulation film of MOSFET, and the ISFET is immersed in aqueous solution, and variation of channel conductance on the basis of potential changes of the sensing section is detected, and the hydrogen ion density in the aqueous solution is determined.

However, the ISFET is low in sensitivity (theoretical maximum sensitivity determined from Nernst equation is 59 mV/pH), and is unstable in output in terms of time, and ion density cannot be detected at high precision. In the field of biochemical measurement, on the other hand, if the sensitivity of the ISFET can be improved, it is expected to be used in detection of presence or absence of, for example, generation of hybridization of oligonucleotide, and determination of base sequence of specimens.

Hybridization analysis is a technique of preparing a single strand nucleic acid (probe) complementary to the nucleic acid (target nucleic acid) to be identified, detected or isolated, detecting whether the single strand nucleic acid of the specimen is hybridized with the probe or not, or measuring the amount of hybridized double strand nucleic acid.

As a method of detecting base sequence of nucleic acid by applying gel electrophoresis in this hybridization analysis, a southern blot technique is known. In this southern blot technique, a double strand DNA fragment of specified length is applied in gel electrophoresis, the gel is immersed in an alkaline solution, and double strands are split by electrophoresis, and formed into single strand with a band. This is transferred on a DNA binding sheet. The sheet is immersed in a hybrid forming solution, and a radioactive probe is added, and heated and hybridized. As a result, it is known which band is bound with which probe, and a band having a base sequence complementary to the probe can be detected. This method is, however, complicated in operation, and it takes much time and cost. It is hence urgently demanded to develop a method of improving the sensitivity in ISFET and capable of applying it in biochemical measurement such as analysis of hybridization.

The invention is devised in the light of the above background, and it is hence a primary object thereof to present a structure of ion type sensor by making use of the principle of detection of ion density changes at high precision, by transferring depth changes of potential well immediately beneath the sensing section on the basis of surface potential changes of the sensing section of the ISFET repeatedly to the drain as electric charge, and accumulating electric charge in the drain, so that a slight change in surface potential of the sensing section can be detected, and an ion density detecting method comprising this sensor structure.

When transfer of electric charge from the source to the drain is repeated n times to accumulate electric charges, the variation of the drain potential is n times, whereas the noise is generally a random value, and changes only $\sqrt{n}$ times, and the S/N ratio is $n/\sqrt{n}=\sqrt{n}$ times, and the sensitivity is higher by this portion. As a result, if the changes are small in the depth of the immediately beneath the potential well on the basis of the change of surface potential of the sensing section, they are accumulated and detected securely, so that the ion density change can be detected at high sensitivity.

The basic structure of the ISFET based on the electric charge accumulation principle has been invented already by the present inventors and disclosed on Sep. 27, 2000 in Japanese Patent Application No. 2000-293669 in the title of "Cumulative type chemical and physical phenomenon detecting apparatus". In the structure disclosed in this application, the gate on the gate insulation film of the MOSFET is divided into two sections, and an ion sensing film (sensing section) is inserted in the split interval to compose an ISFET, in which a reset transistor for resetting the drain potential is incorporated.

It is hence an object of the invention to present an FET type sensor and an ion density detecting method capable of detecting presence or absence of a specimen in sample or its content accurately, by fixing a substance reacting or binding with the specimen in sample or acting as a catalyst for reaction of the specimen in a sensing section of ISFET, and accurately detecting the change of ion density on the basis of reaction or binding.

It is another object of the invention to present an FET type sensor and a base sequence detecting method capable of determining the base sequence simply, quickly and at low cost, without increasing the DNA by PCR method, by fixing a target nucleic acid and a complementary single-strand nucleic acid in a sensing section of ISFET, detecting accurately, if changes are slight, the potential of the surface of a semiconductor substrate immediately beneath the sensing section on the basis of changes of surface potential of the sensing section, and detecting presence or absence of generation of hybridization between the nucleic acid in the sample and the single-strand nucleic acid at high sensitivity.

It is a further object of the invention to present an ion sensor comprising a plurality of said ISFETs capable of detecting presence or absence of generation of hybridization in a plurality at once, and determining the base sequence of nucleic acid in samples simply and in a short time.

On the other hand, in the invention, since the ISFET has a faster transfer speed in the flow of electrons by n-type channel than in the flow of holes by p-type channel, the npn structure is employed, and hence the structural demerits of the ISFET are overcome by solving the problems, that is, the depth of the potential well generated beneath the sensing section between the input and output gates depends on the magnitude of relative plus ion/minus ion density acting on the sensing section, and the well is shallow or not formed when the plus ion density is low or the minus ion density is dominant.

SUMMARY OF THE INVENTION

To solve the first problem, this invention presents an FET type sensor comprising;

an input diode section and a floating diffusion section consisting of a diffusion region reverse to the substrate in conductivity type, formed across a specified interval on the face side of a P type or N type semiconductor substrate, an input gate and an output gate fixed by way of an insulation film, at positions on the substrate surface corresponding to the initial end and terminal end of a conductive channel formed from the input diode section to the floating diffusion section, a sensing section consisting of an ion sensitive film fixed by way of an insulation film, at a position on the substrate surface corresponding to the middle of the channel, a reset gate fixed by way of an insulation film, at a position on the substrate surface continuous to the side remote from the channel in the floating diffusion section, and a reset diode section consisting of a diffusion region reverse to the substrate in conductivity type, formed on the substrate surface at a side remote from the floating diffusion section in the reset gate, wherein a substance reacting or binding with a specimen in the sample in the sensing section or acting as catalyst for reaction of the specimen is fixed in the sensing section, and the electric charge accumulated in the floating diffusion section after resetting of the potential is detected as potential change, depending on the depth of the potential well changed according to the ion density acting on the sensing section and the number of times of seepage from the potential well.

To solve the second problem (detection of hybridization), this invention is characterized by using a single-strand nucleic acid complementary to the specimen, as a substance to be fixed in the sensing section. Hence, without increasing the DNA by PCR method or the like, the presence of target nucleic acid in the sample can be detected simply, quickly and at low cost, so that the base sequence can be determined easily.

To solve the third problem (detection of plurality of hybridizations), this invention presents an FET type sensor comprising a plurality of FET type sensor elements each consisting of;

an input diode section and a floating diffusion section consisting of a diffusion region reverse to the substrate in conductivity type, formed across a specified interval on the face side of a P type or N type semiconductor substrate, an input gate and an output gate fixed by way of an insulation film, at positions on the substrate surface corresponding to the initial end and terminal end of a conductive channel formed from the input diode section to the floating diffusion section, a sensing section consisting of an ion sensitive film fixed by way of an insulation film, at a position on the substrate surface corresponding to the middle of the channel, a reset gate fixed by way of an insulation film, at a position on the substrate surface continuous to the side remote from the channel in the floating diffusion section, and a reset diode section consisting of a diffusion region reverse to the substrate in conductivity type, formed on the substrate surface at a side remote from the floating diffusion section in the reset gate, all being formed parallel on a same semiconductor substrate, wherein the input gate, reset gate, and reset diode of each sensor element are formed commonly from the single input gate, single reset gate, and single reset diode extending to all elements.

To solve the fourth problem (overcoming the structural restriction of n channel type FET), this invention presents an FET type sensor comprising;

an input diode section and a floating diffusion section consisting of a diffusion region reverse to the substrate in conductivity type, formed across a specified interval on the face side of a P type or N type semiconductor substrate, an input gate and an output gate fixed by way of an insulation film, at positions on the substrate surface corresponding to the middle and terminal end of a conductive channel formed from the input diode section to the floating diffusion section, a sensing section consisting of an ion sensitive film fixed by way of an insulation film, at a position on the substrate surface corresponding to the input end of the channel, a reset gate fixed by way of an insulation film, at a position on the substrate surface continuous to the side remote from the channel in the floating diffusion section, and a reset diode section consisting of a diffusion region reverse to the substrate in conductivity type, formed on the substrate surface at a side remote from the floating diffusion section in the reset gate, wherein it is designed to detect the electric charge accumulated in the floating diffusion section after resetting of the potential as potential change, depending on the depth of the potential well changed according to the ion density acting on the sensing section and the number of times of seepage from the potential well.

In the foregoing FET type sensor, the depth (capacity) of the potential well is set in a mechanism in which the height of the inlet (the electric charge limit level) of the potential well formed stably at the lower side of the inlet gate is given by the potential of the sensing section positioned between this gate and the input diode (charge supply unit).

In this FET type sensor, the depth of potential well by ion density of sample is not determined by the bottom level as in the basic type, but determined by the input level, and when fixing a substance reacting or binding with a specimen or acting as catalyst for reaction of the specimen in the sensing section, if the fixed substance is a single-strand nucleic acid complementary to the specimen, presence or absence of generation of hybridization between the nucleic acid in the sample and its single-strand nucleic acid can be surely detected. In this case, generation of hybridization becoming higher in the minus ion density as binding of negatively charged nucleic acids can be detected at high sensitivity.

In the FET type sensor comprising a plurality of said FET type sensor formed parallel on a same semiconductor substrate, when the input gate, reset gate, and reset diode of each sensor element are formed commonly from the single input gate, single reset gate, and single reset diode extending to all sensor elements, it is evident that the nucleic acid structure in the sample can be measured.

In this invention, moreover, by disposing the cumulative type ISFET of basic structure and the cumulative type ISFET of a structure defining the potential well inlet level in the sensing section as the means for solving the fourth problem, parallel on a same substrate, it can be formed as an FET type sensor of wide measuring range covering both plus ions and minus ions, comprising an input diode section and a floating diffusion section consisting of a diffusion region reverse to the substrate in conductivity type, formed across a specified interval on the face side of a P type or N type semiconductor substrate, wherein said floating diffusion section is divided into a first drain and a second drain, the input diode section is used as a common source having a portion corresponding to these two divisions, and first and second mutually parallel channels are formed in the substrate surface side between the source and drain, a common reset diode consisting of a diffusion region reverse to the substrate in conductivity type is formed on the side of the floating diffusion section for composing the first and second drains, opposite to the two channels, across a small interval from said floating diffusion section, and a common reset gate is fixed by way of an insulation film on the substrate surface side in this small interval, an input gate and an output gate are fixed by way of an insulation film, at positions on the substrate surface corresponding to the both ends of the first channel, and a sensing section consisting of an ion sensitive film is fixed by way of an insulation film, at a position on the substrate surface corresponding to the middle of the first channel, an input gate and an output gate are fixed by way of an insulation film, at positions on the substrate surface corresponding to the middle and terminal end of the second channel, and a sensing section consisting of an ion sensitive film is fixed by way of an insulation film, at a position on the substrate surface corresponding to the initial end of the second channel, and it is designed to detect the electric charge accumulated in the first and second drains of the floating diffusion section after resetting of the potential as potential change, depending on the depth of the potential well changed according to the ion density acting on each sensing section on the first channel and second channel and the number of times of seepage from the potential well.

Further, this invention forms a plurality of the composite type sensors on a same semiconductor substrate, and detects a plurality of complementary nucleic acid structures in the specimen efficiently and simultaneously.

By using the ion sensor having such constitution, the invention opens a new dimension in the biochemical field, in particular, for judging the presence of specific organisms in samples or nucleic acid having a base sequence specific to disease, detecting presence or absence of organisms or diseases easily and securely, and content of organisms, and measuring endocrine-disrupting chemicals, dioxins and related substances.

This invention also presents a method of using an FET type sensor comprising an input diode section and a floating diffusion section consisting of a diffusion region reverse to the substrate in conductivity type, formed across a specified interval on semiconductor substrate, a sensing section consisting of an ion sensitive film exposed on the surface and fixed by way of an insulation film, at a position on the substrate surface corresponding to the middle or initial end of a conductive channel to be formed on the substrate surface layer in the interval, wherein a potential well varying in the depth according to the ion density acting on the sensing section is formed in the middle of the conductive channel, and the electric charge according to the seepage amount from the potential well is measured in the floating diffusion section, and thereby from the measured value of the electric charge, it is designed to detect presence or absence of hybridization of single-strand nucleic acid fixed in relation to the sensing section and the specimen, or the conformity between the antigen or antibody fixed in relation to the sensing section and the specimen.

This invention also presents a detecting method of base sequence by using an FET type sensor comprising an input diode section and a floating diffusion section consisting of a diffusion region reverse to the substrate in conductivity type, formed across a specified interval on semiconductor substrate, a sensing section having a gold film exposed on the surface and fixed by way of an insulation film, at a position on the substrate surface corresponding to the middle or initial end of a conductive channel to be formed on the substrate surface layer in the interval, wherein a potential well varying in the depth according to the ion density acting on the sensing section is formed in the middle of the conductive channel, and the electric charge according to the seepage amount from the potential well is measured in the floating diffusion section, at least one comparing electrode is fixed by way of an insulation film on the substrate surface near the sensing section, a terminal radical of single-strand nucleic acid complementary to a DNA specimen is fixed in the gold film, a same sample solution is supported in a region including the sensing section and comparing electrode, and the seepage electric charge amount from the potential well is measured on the basis of the potential of the comparing electrode, thereby detecting presence or absence of hybridization of the single-strand nucleic acid and specimen.

This invention moreover presents a detecting method of base sequence by using an FET type sensor comprising an input diode section and a floating diffusion section consisting of a diffusion region reverse to the substrate in conductivity type, formed across a specified interval on semiconductor substrate, a sensing section having a gold film exposed on the surface and fixed by way of an insulation film, at a position on the substrate surface corresponding to the middle or initial end of a conductive channel to be formed on the substrate surface layer in the interval, wherein a potential well varying in the depth according to the ion density acting on the sensing section is formed in the middle of the conductive channel, and the electric charge according to the seepage amount from the potential well is measured in the floating diffusion section, a terminal radical of single-strand nucleic acid complementary to a DNA specimen is fixed in the gold film, a sample solution is supported in the sensing section, a measuring electrode positioned directly above the gold film, and a comparing electrode disposed by deviating a distance slightly so as not to affect electrically the nucleic acid fixed on the gold film are provided above the sensing section, these two electrode are lowered to immerse in the sample solution, a potential enough to adsorb the DNA terminal radical hybridized on the nucleic acid fixed on the gold film by the measuring electrode is applied to these two electrodes, a current flowing between the measuring electrode and the grounding potential is measured on the basis of the current flowing in the comparing electrode, and presence or absence of hybridization between the single-strand nucleic acid and specimen is detected.

Still more, this invention presents a detecting method of base sequence by using an FET type sensor comprising an input diode section and a floating diffusion section consisting of a diffusion region reverse to the substrate in conductivity type, formed across a specified interval on semiconductor substrate, a sensing section consisting of an ion sensitive film fixed by way of an insulation film, at a position on the substrate surface corresponding to the middle or initial end of a conductive channel to be formed on the substrate surface layer in the interval, wherein a potential well varying in the depth according to the ion density acting on the sensing section is formed in the middle of the conductive channel, and the electric charge according to the seepage amount from the potential well is measured in the floating diffusion section, a sample fixing gold electrode is fixed by way of an insulation film on the substrate surface near the sensing section, and a terminal radical of single-strand nucleic acid complementary to a DNA specimen is fixed in the gold electrode, a same sample solution is supported in a region including the sensing section and the gold electrode, and an intercalating agent for invading into DNA double helices to be formed by hybridizing to the nucleic acid fixed on the gold electrode is added, a specified voltage is applied to the gold electrode to vary the PH of the sample solution on the basis of the oxidizing and reducing current flowing between the intercalating agent between the DNA double helices and the gold electrode, and seepage charge amount from the potential well as the depth corresponding to the PH change is measured on the basis of the potential of the comparing electrode, thereby detecting presence or absence of hybridization between the single-strand nucleic acid and specimen.

For executing the above four methods, this invention comprises a pair of FET type sensors disposed on a same semiconductor substrate, an electrochemically inert outer peripheral wall enclosing the peripheral edges of the pair of FET type sensors in batch, and a partition wall partitioning between the sensors with the both ends internally contacting with the outer peripheral wall, wherein the sample solutions contained in each sensor do not communicate with each other, a target substance reacting with the specimen is fixed on the one sensor only, out of the two adjacent sensors on the same substrate, and nothing is fixed on the other sensor, and by using the same sample solution, the time-course drifts of solution or substance are measured by the other sensor, and the drift value is subtracted from the measured value of the one sensor, and thereby the compatibility of the specimen and target substance can be detected accurately.

DETAILED DESCRIPTION OF THE INVENTION

Embodiments of the invention are described below while referring to the accompanying drawings.

Embodiment 1

Figure 1:
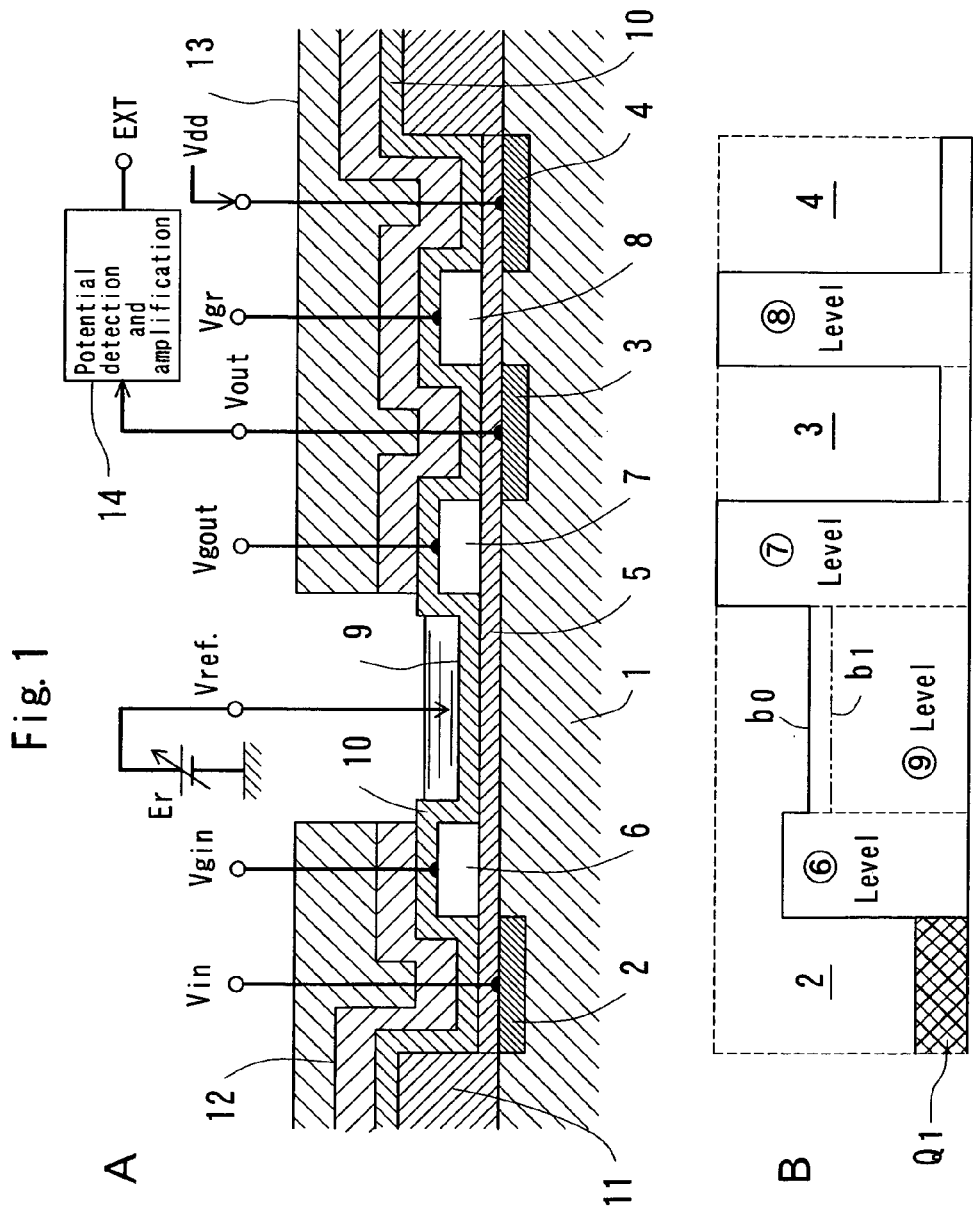
FIG. 1 is a sectional view (A) and a schematic view (B) showing a potential state of FET type sensor in Embodiment 1 of this invention.
Figure 2:
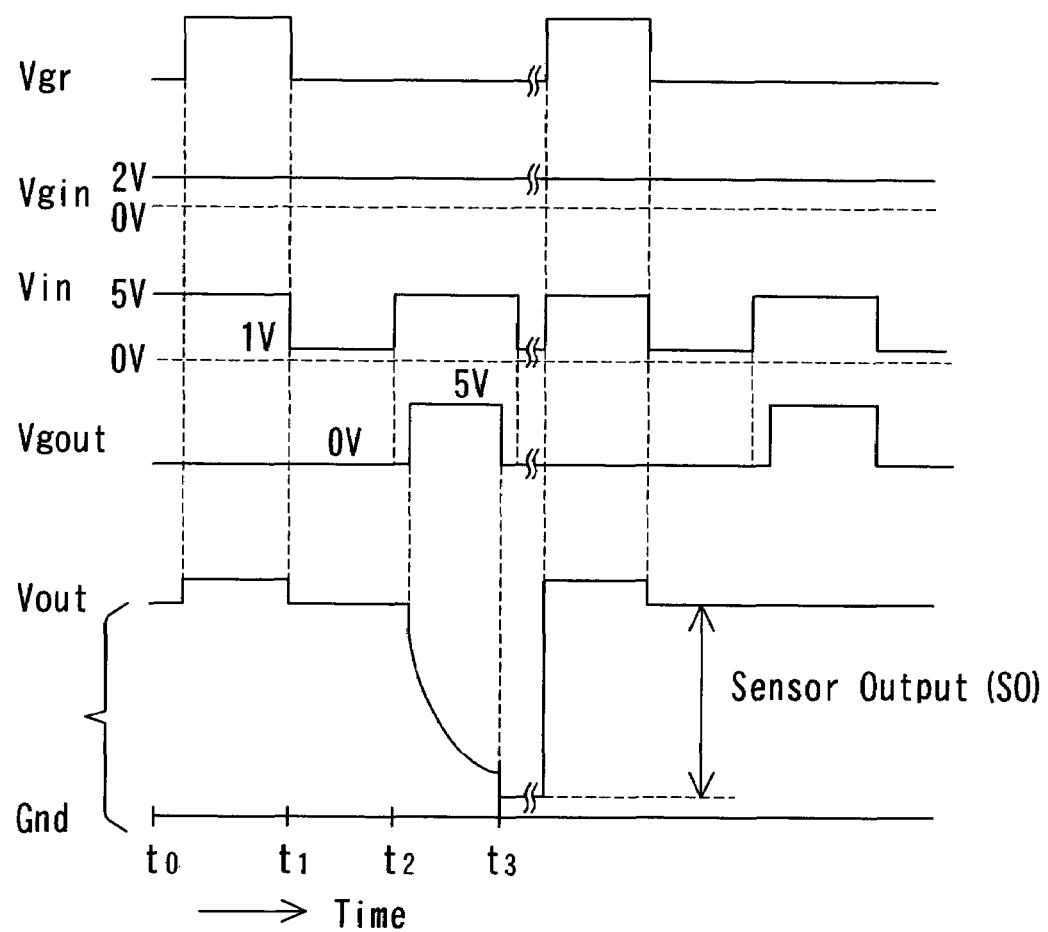
FIG. 2 is a voltage waveform diagram showing timing of applying voltage to parts and detecting output potential in the FET type sensor of this invention.

FIG. 1 is a sectional view (A) and a schematic view (B) showing a basic potential state of FET type sensor in Embodiment 1 of the invention, and FIG. 2 is a schematic view sequentially showing each potential state in the operating state. In FIG. 1A, reference numeral 1 is typically a p− type semiconductor substrate made Of silicon, and the face side of the semiconductor substrate 1 includes an input diode 2 and a floating diffusion section (FD) 3 as charge supply sections composed of n+ type diffusion layer formed across a specific interval, and a reset diode 4 is formed at a further small Interval from the floating diffusion section 3. On the semiconductor substrate 1, in this case, an insulation film 5 made of SiO2 or Si3N4 is formed, including on the n+ type diffusion layer.

On the surface of the semiconductor substrate 1 between the input diode 2 and floating diffusion section 3, a conductive channel (n type inversion layer) is formed in relation to the gate structure described below, and hence, using the input diode 2 as the source and the floating diffusion section 3 as the drain, an FET type sensor is composed. On the insulation film 5, an input gate 6 is formed at a position adjacent to the input diode 2 corresponding to the channel initial end, and an output gate 7 is formed at a position adjacent to the floating diffusion section 3 corresponding to the channel terminal end, respectively, by vapor deposition layer composed of polysilicon or aluminum, and further a reset gate 8 is formed between the floating diffusion section 3 and reset diode 4 similarly by a vapor deposition layer.

On the top of the input gate 6, output gate 7, and reset gate 8, and on the insulation film 5 outside of the gate supporting these gates, a coating film 10 typically made of Si3N4 vapor deposition layer is formed. The Si3N4 film is more dense in structure and smaller in oxygen diffusion coefficient as compared with the SiO2 film, and it forms by itself a favorable ion sensitive film as a sensing section 9 in a recess formed between the input and output gates 6 and 7. As the ion sensitive film, aside from Si3N4, further, SiO2 or Au may be used. In the ion sensitive film of the sensing section 9, a substance reacting or binding with the specimen in the sample, or serving as catalyst for reaction with specimen is fixed, such as enzyme, antibody, microorganism, or nucleic acid (not shown).

Preferably, on the surface of the semiconductor substrate outside of the input diode 2 and floating diffusion section 3, a channel stopper for decreasing the leak current is provided, by using, in this case, a p+ diffusion section (not shown) higher in acceptor density than the p− substrate and equal to the donor density of n+ diffusion sections 2 and 3, thereby preventing the electric charge from leaking from the input diode 2 and floating diffusion section 3 to outside of the channel.

On the surface of the semiconductor substrate 1, outside of the input diode 2 and reset diode 4, a relatively thick mask layer 11 of silicon oxide film or the like same as the insulation film 5 is formed, and the vapor deposition film 10 forming the sensing section 9 also covers this mask layer 11, and further on the vapor deposition layer 10, except for the sensing section 9, a protective film 12 made of, for example, phosphor glass, and an outer film 13 on the protective film 12 are formed to cover and flush the surface.

From the left side of the drawing, on the top of the input diode 2, input gate electrode 6, output gate electrode 7, floating diffusion section 3, reset gate 8, and reset diode 4, electrode leads of aluminum or the like are formed, and a voltage according to the measuring sequence is applied or detected (the potential of the floating diffusion section 3) through these electrode leads. The floating diffusion layer 3 is connected to the input of a potential detecting and amplifying circuit 14 including a source follower amplifier capable of incorporating an electrode lead terminal Vout into a same semiconductor substrate 1.

FIG. 2 shows the timing of application of voltage to the parts through the electrode leads according to the measuring sequence of ion density. First, in the sensing section 9, as shown in FIG. 1A, reference voltage Vref is applied from a variable voltage source Er into the sample solution contained in the sensing section 9 or in the sample bath immersing the sensing section 9, and an ion sensitive film potential is generated by ionization of the sample solution by this application.

In the application circuit (not shown) of direct-current voltage to the electrode leads other than the sensing section 9, in the initial state (t0 to t1) shown in FIG. 2, an reverse bias voltage Vin of about 5 V is applied to the input diode 2 which is the charge feeder, and a direct-current voltage Vgin (about 2 V) is applied to the input gate 6, while the output gate 7 is maintained at Vgut=0. In this case, slightly later, a reset voltage pulse Vgr is applied to the reset gate 8 for about several milliseconds, and the potential Vout of the adjacent floating diffusion section 3 is slightly elevated as being pulled up by the voltage Vdd in this period, but it is assumed herein that there is no change in the potential before and after, that is, no accumulation of electric charge.

Measuring steps of ion density detection are explained below while referring to FIG. 1B and FIG. 3. FIG. 1B shows the potential and electric charge of parts of the FET type sensor in this embodiment in the initial state, corresponding to the parts in FIG. 1A, and when a reverse bias voltage to the input diode 2 is 5 V, the residual charge Q1 is slight in this portion, stopping below the barrier level by the direct-current voltage Vgin (about 2.0 V) of the input gate 6. Reference voltage Vref in the sensing section 9 is an initial set value for keeping constant the surface potential of the semiconductor substrate 1 immediately beneath the sensing section 9 through the sample solution (usually aqueous solution), thereby determining the depth (bottom level) b0 of the potential well, but at this moment, there is no charge flowing in by surpassing the gate barrier.

Reaching time t1, reverse bias voltage vin of the input diode 2 is lowered to 1 V for several milliseconds until reaching time t2. This decline of the reverse bias voltage brings about a relative supply of electric charge, and its storage upper limit exceeds the input gate barrier of about 2 V, and reaches closer to the barrier upper end by the output gate 7 of 0 V. Accordingly, the supplied charge (electron in this case) flows into the semiconductor surface below the input diode 2 and input gate 6, and also flows into the potential well on the semiconductor surface below the sensing section 9. This state (initial charge supply) is as shown in FIG. 3A.

Reaching time t2, reverse bias voltage 5 V to the input diode 2 is recovered, and maintained for several milliseconds. As shown in FIG. 3B, a considerable portion of charge Q2 is returned to the power source circuit, and the charge collected above the potential well beneath the sensing section 9 is controlled by the barrier of the input gate 6 and returns to the input diode 2, and is added to the reflux to the power source circuit, and the electric charge corresponding to the depth of the bottom level b0 is left over in the potential well of the barrier side. The amount of charge remaining in the potential well corresponds to the variation of the surface potential of the sensing section 9 according to the ion density of the aqueous solution.

As the plus ion density in the aqueous solution contained in the sensing section 9 rises, the surface potential of the sensing section 9 changes, and the surface potential of the semiconductor substrate 1 immediately beneath the sensing section 9 becomes lower than the initial set value. As a result, the bottom level of the potential well becomes deep, for example, to a level of b1 shown in the diagram. When the plus ion density declines or the minus ion density hikes, evidently, the bottom level elevates.

When voltage Vgout of 5 V is applied to the output gate 7, this output gate 7 is opened, and the charge is transferred to the preliminarily reset floating diffusion section 3 (FIG. 3C). Herein, by setting the capacity of the floating diffusion section 3 smaller than the capacity of the sensing section 9, as shown in the diagram, the potential variation of the floating diffusion section 3 increases. In FIG. 2, the potential change of the floating diffusion section 3 initially drops steeply from the stationary potential Vout in the state without charge along with the flow of the charge, and then changes moderately and is finally stabilized at the potential close to the ground potential.

Thus, after transfer of charge, the voltage Vgout applied to the output gate 7 declines to 0 V, and the output gate 7 is closed (FIG. 3D). Thus, the cycle of t1 to t3 is repeated, and the steps of supply of charge from the input diode 2 to the potential well, control by the input gate 6, and transfer of the charge remaining in the potential well to the floating diffusion section 3 by opening of the output diode 7 are executed sequentially, and the transferred charges are successively accumulated in the floating diffusion section 3.

This accumulated charge amount, as a large potential change, becomes a sensor output signal SO (FIG. 2) to be entered in the potential detecting and amplifying circuit from the output terminal Vout of the floating diffusion section 3 shown in FIG. 1A. After reading of the potential, the adjacent reset gate 8 is opened by application of open gate voltage Vgr, and the floating diffusion section 3 discharges the accumulated charge through the conductive channel to the reset diode 4 connected at the potential +Vdd, and is set again to the initial potential (FIG. 3E).

In the FET type sensor thus composed, when transferred n times to the floating diffusion section 3, the change is increased n times as compared with the case without time accumulation, but the noise is changed only $\sqrt{n}$ times, and the S/N ratio is increased by $\sqrt{n}$ times, and hence the sensitivity is raised as mentioned above. Therefore, if the change is small in the depth of the potential well immediately beneath the sensing section 9 on the basis of the change of the surface potential of the sensing section 9, this change is detected securely, and the change of ion density on the basis of reaction or binding of the specimen with the fixing body, or the change of ion density on the basis of the catalytic reaction of the fixing body can be detected at high sensitivity.

In this FET type sensor, when enzyme is fixed in the sensing section 9, urea, glucose, penicillin, acetyl choline, alcohol or the like can be detected. For example, when detecting urea, urease is used as the enzyme, and changes of hydrogen ion density due to decomposition reaction of urea by urease can be detected If a single-strand nucleic acid (probe) complementary to the specimen (target nucleic acid) is fixed in the sensing section 9, presence or absence of generation of hybridization between the specimen and probe can be detected at high sensitivity. Therefore, without increasing the DNA by PCR method, presence or absence of generation of hybridization can be detected simply, quickly and at low cost, and the base sequence can be determined.

Further, a plurality of FET type sensors of the Embodiment 1 may be formed on a same semiconductor substrate 1, and by fixing single-strand nucleic acids complementary to the plurality of target nucleic acids individually in the sensing section 5 of each ISFET, a plurality of occurrences of hybridization can be detected in batch, and the base sequence of the nucleic acid of the sample can be determined simply and in a short time.

Embodiment 2

Figure 3:
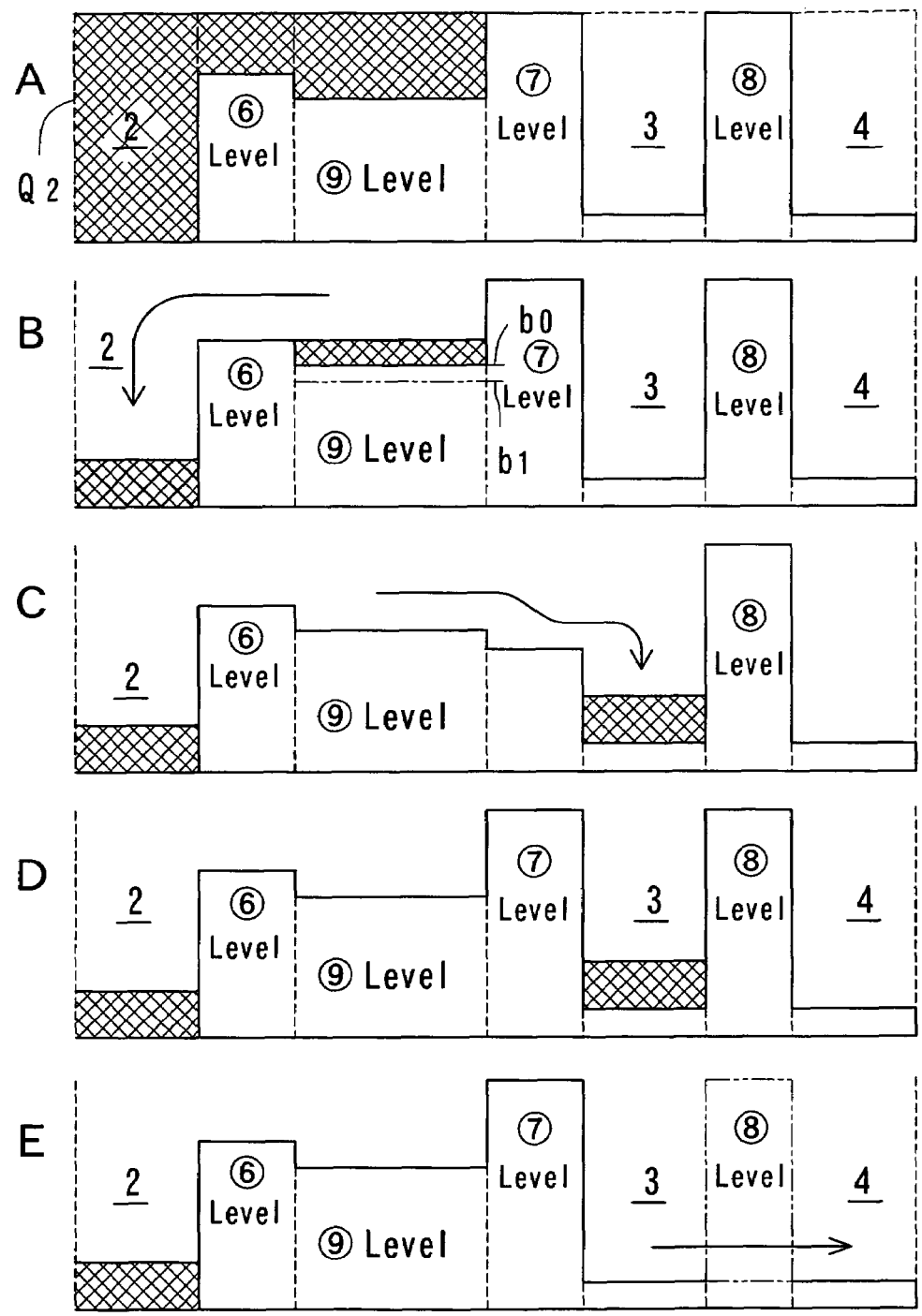
FIG. 3 is a schematic view showing transition of potential state of FET type sensor in Embodiment 1 of this invention.
Figure 4:
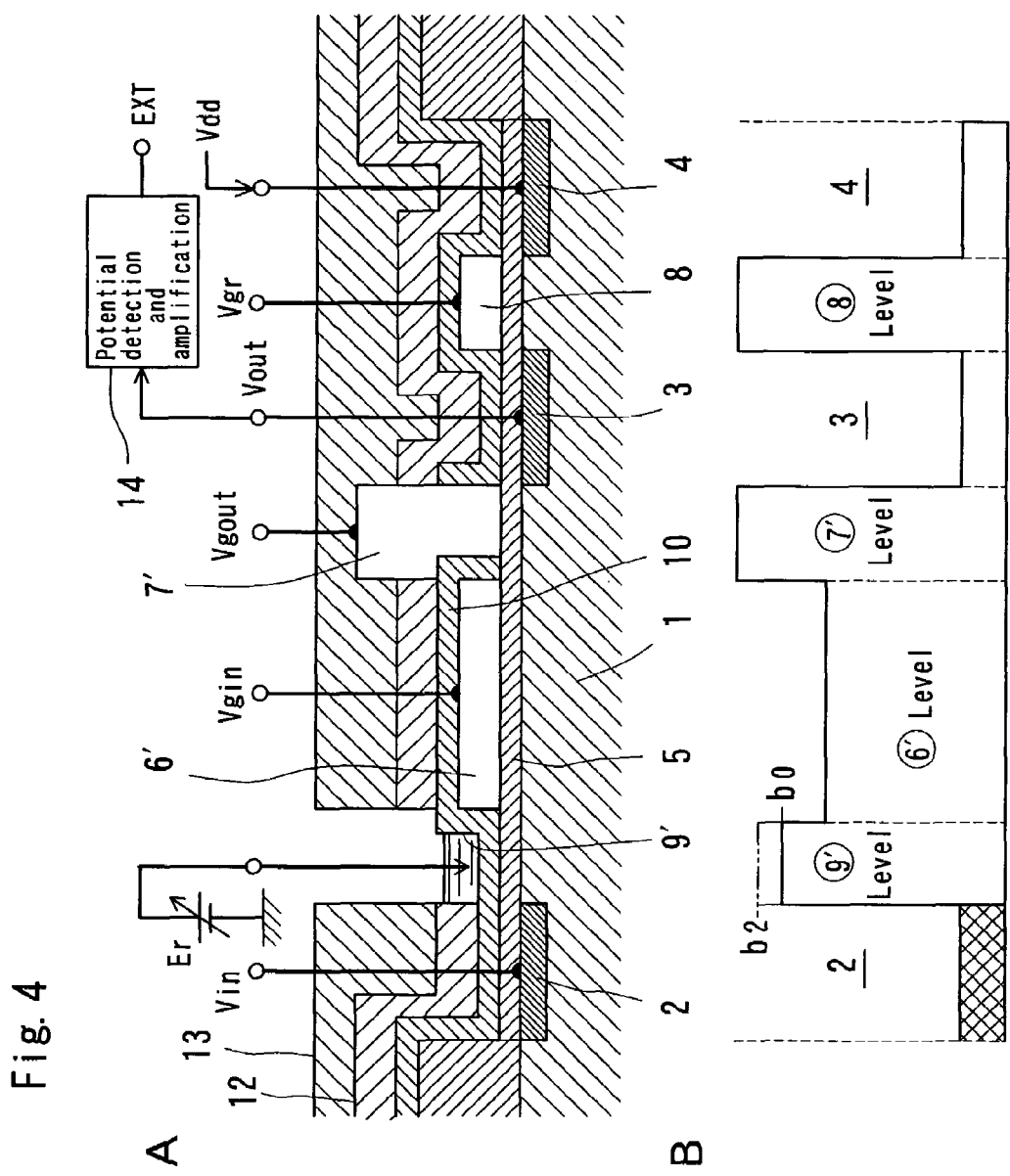
FIG. 4 is a sectional view (A) and a schematic view (B) showing a potential state of FET type sensor in Embodiment 2 of this invention.
Figure 5:
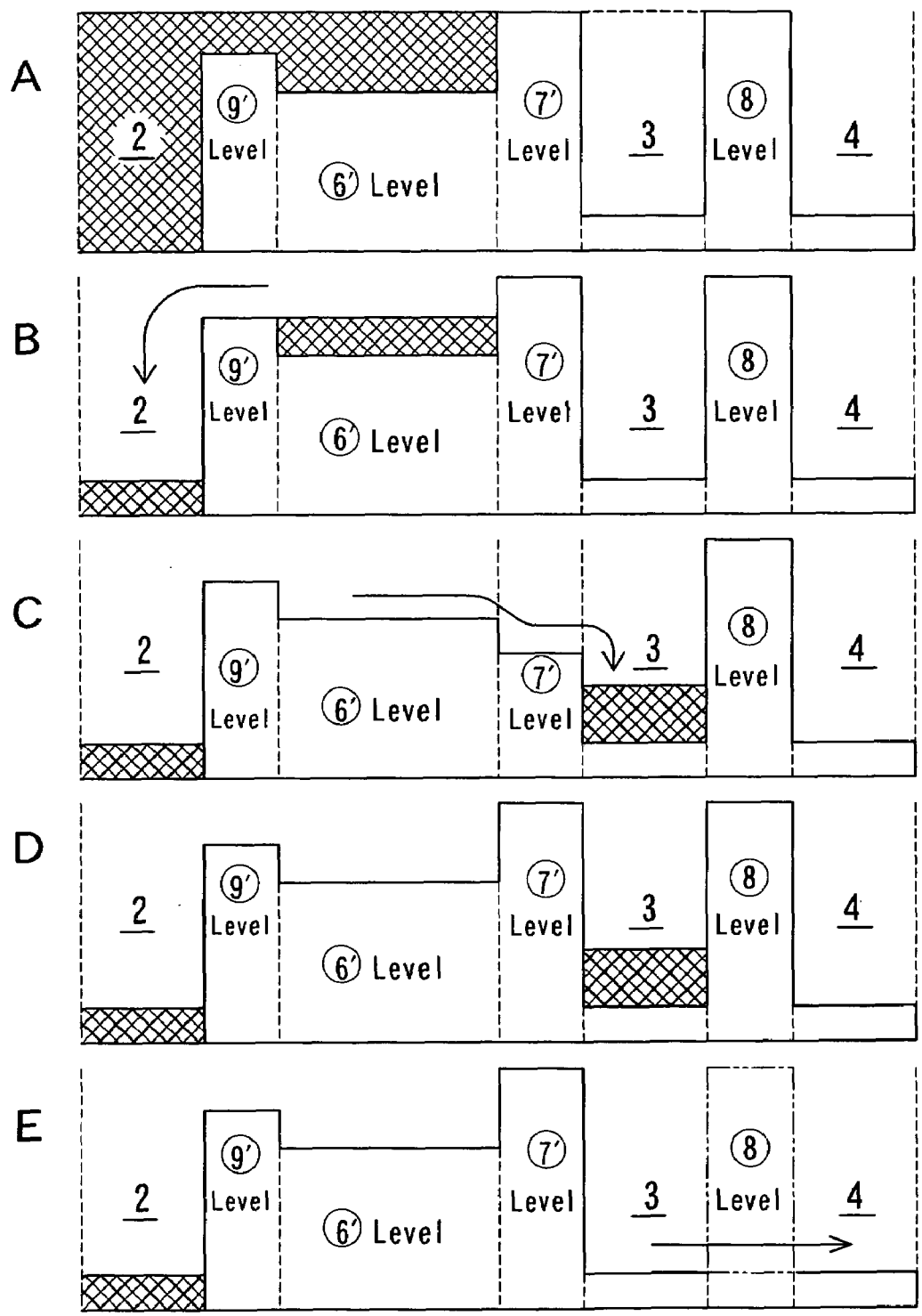
FIG. 5 is a schematic view showing transition of potential state of FET type sensor in Embodiment 2 of this invention.

FIG. 4 is a sectional view (A) and a schematic view (B) showing a basic potential state of FET type sensor in Embodiment 2 of the invention, and FIG. 5 is a schematic view showing the transition of potential state and accumulated charge. In the drawings, same parts as in FIG. 1 and FIG. 3 are identified with same reference numerals, and the explanation is simplified or omitted.

The FET type sensor in Embodiment 2 is similar to that in Embodiment 1, that is, at the surface side of a P− type semiconductor substrate, an input diode 2 and a floating diffusion section 3 comprising a diffusion region reverse to the substrate in conductivity, that is, N+ type are formed across a specific interval, and a reset diode 4 is also formed, and a reset gate 8 is formed on an insulation film 5 between the floating diffusion section 3 and reset diode 4, thereby forming a reset transistor for the floating diffusion section 3, and the structure above the insulation film 5 between the input diode 2 and floating diffusion section 3 is different from Embodiment 1 as described below.

An input gate 6' and an output gate 7' are fixed on insulation films 5 corresponding to the middle and terminal end of the conductive channel to be formed between the input diode 2 and the floating diffusion section 3, and in order to form the both gates 6' and 7' closely to each other, the relatively narrow and high output gate 7' is insulated from the gate 6' by coating film 10 covering the adjacent side of the relatively wide input gate 6'. The bottom of the output gate 7' contacts with the insulation film 5 on the semiconductor substrate 1, and its upper part penetrates through the coating film 10 and protective film 12, and the upper end has enough height to be positioned within an outer film 13.

At a position on the substrate surface between the input diode 2 and input gate 6' thus formed, that is, at a position corresponding to the input end of an inverting channel to be formed, the insulation film 5 forming the bottom is provided together with a sensing section 9' forming a recess as being enclosed by the insulation film 5 at the input gate 6' side as the ion sensitive film, the coating film 10 at the input diode 2 side, and the section of the protective film 12.

Hereinafter, the detecting method of ion density by using this ion sensor is explained.

Same as in Embodiment 1, first, reference voltage Vref is applied in the aqueous solution in the sensing section 9' from a variable voltage source, and the surface potential of the semiconductor substrate 1 immediately beneath the sensing section 9 is made constant. This is the initial set value of the potential well inlet. Then, as shown in FIG. 2, a proper direct-current voltage Vgin (for example, 2.0 V) is applied in the input gate 6', and the surface potential of the semiconductor substrate 1 immediately beneath it is fixed, and a reverse bias voltage Vin=5 V is applied to the input diode 2 as the charge supply unit, and voltage Vgr is applied to the reset gate 8, and the initial value of the potential of the floating diffusion section 3 is set. At this time, the voltage of the output gate 7' is zero volt.

Voltage Vin of 5 V in the input diode 2 is a sufficient reverse bias, and the remaining charge in the gate is very slightly suppressed as shown in FIG. 4B, and the upper end of this charge pool does not reach the level of the sensing section 9', and does not invade after the section 9'. In this case, when the minus ion density in the aqueous solution becomes higher, the surface potential of the sensing section 9' changes, and the surface potential of the semiconductor substrate 1 immediately beneath the sensing section is further elevated from said initial set value b0 (to be b2 in FIG. 4B), when the minus ion density declines or the plus ion density hikes, to the contrary, the surface potential rises from b0 (not shown).

When the voltage Vin applied to the input diode 2 drops from 5 V to 1.0 V, the reverse bias is lessened, and the charge pool increases by the corresponding portion, and its level exceeds the substrate surface potential b0 (potential well input level) immediately beneath the sensing section 9', and the charge from the input diode 2 is supplied into the potential well immediately beneath the input gate 6' (FIG. 5A).

Again, when the voltage vin applied to the input diode 2 is raised to 5 V, the charge is controlled by the level of the surface potential immediately beneath the sensing section 9', and the electric charge is left over by the portion of the capacity of the potential well at this level, and the other charge is returned to the power source, through the input diode 2, leaving the portion to be left over in the diode 2 (FIG. 5B). In this case, too, the amount of charge left over in the potential well varies with the minus ion density, and it is evident that the variation of the surface potential of the sensing section 9' is converted into this amount of charge.

When voltage Vgout of 5 V is applied to the output gate 7', this gate 7' is opened, and the charge is transferred to the floating diffusion section 3 maintained preliminarily at a reset potential (FIG. 5C).

After the transfer of the charge, the voltage Vgout applied to the output gate 7' drops to 0 V, and the output gate 7' is closed (FIG. 5D).

By repeating the process from FIG. 4B to FIG. 5D, the variation of surface potential of the sensing section 9' is accumulated as the charge in the floating diffusion section 3. The potential change accumulated in the floating diffusion section 3 is fed as Vout into the potential detecting and amplifying circuit 14, and is indicated and recorded, and used for other process.

After reading of the potential of the floating diffusion section 3, reset gate voltage Vgr is applied to the reset gate 8, and the charge of this section 3 is guided into the reset diode 4 connected at +Vdd, and is further absorbed in the power source, and the initial value Vout is set again.

In the potential well inlet adjustment type sensor thus composed, after transfer of n times, as compared with the case without time accumulation, evidently, the S/N ratio is increased by $\sqrt{n}$ times and the sensitivity becomes higher. Therefore, if the change is small in the depth of potential well immediately beneath the sensing section 9' on the basis of change of surface potential of the sensing section 9', it can be detected securely, and the change of ion density on the basis of reaction or binding of the specimen with the fixing body, or the change of ion density on the basis of the catalytic reaction of the fixing body can be detected at high sensitivity.

Supposing the sensor of Embodiment 1 shown in FIG. 1 and FIG. 3, in this sensor, when the minus ion density becomes higher, or the plus ion density becomes lower, the depth of the potential well for storing the charge becomes shallow or nil, and hence the amount of charge transferred and remaining in the floating diffusion section 3 is decreased or eliminated.

In Embodiment 2, however, when the substrate surface potential immediately beneath the sensing section 9' adjacent to the input diode 2 is raised, and the difference is increased from the substrate surface potential immediately beneath the adjacent input gate 6, and the potential well is formed in the portion immediately beneath this input gate 6, and therefore to the sample of relatively high minus ion density, the detection sensitivity is higher than in Embodiment 1, or a sample not detectable in Embodiment 1 can be detected. Therefore, when a probe complementary to the specimen is fixed in the sensing section 9', generation of hybridization becoming higher in minus ion density as binding of negatively charged nucleic acids can be detected at higher sensitivity.

By using the ion sensor in Embodiment 2, for example, by using a nucleic acid complementary to a nucleic acid having a specific base sequence of a specific diseases such as Alzheimer disease or diabetes mellitus, and fixing it as a probe in the sensing section 9', and detecting presence or absence of hybridization of the probe and the nucleic acid in the sample, if hybridization is detected, it is known that the sample contains the nucleic acid having such specific base sequence, so that presence or absence of disease can be detected easily and securely.

Further, by using the ion sensor in Embodiment 2, by using a nucleic acid complementary to a nucleic acid having a specific base sequence of a specific microorganism, and fixing it as a probe in the sensing section 9', and detecting presence or absence of hybridization of the probe and the nucleic acid in the sample, it is known whether or not the sample contains the nucleic acid having such specific base sequence, so that presence or absence and the content of microorganism in the sample can be detected easily and securely.

Moreover, a plurality of FET type sensors of Embodiment 2 may be formed on a same semiconductor substrate 1, and by fixing single-strand nucleic acids complementary to the plurality of target nucleic acids individually in the sensing section 9' of each ISFET, a plurality of occurrences of hybridization can be detected in batch, and the base sequence of the nucleic acid of the sample can be determined simply and in a short time.

In the foregoing Embodiments 1 and 2, the enzyme or nucleic acid is fixed in the sensing sections 9, 9' of the FET type sensor of this invention for detecting urea or presence or absence of hybridization, but the objects of measurement are not limited to these examples, and various specimens can be detected by fixing antibodies, microorganisms and other fixing bodies in the sensing sections 9, 9'. Moreover, these embodiments discloses the detecting of presence or absence of specific diseases or specific microorganism by using the detection of hybridization, but the scope of application is not limited to these examples alone.

Another Embodiments

In the foregoing Embodiments 1 and 2, it is described that the first type of FET type sensor featured with a reset transistor function and the sensing section formed between the input and output gates, and second type of FET type sensor featured with a reset transistor function and the sensing section formed between the input diode and input gate, in which the input and output gates are set closely to each other and shifted to the output side, and such sensor is used alone, or a plurality of the same type FET type sensors are used. However, in the other Embodiment of this invention, by combining the first and second type of FET type sensors, a new third type of FET type sensor may be also composed.

Figure 6:
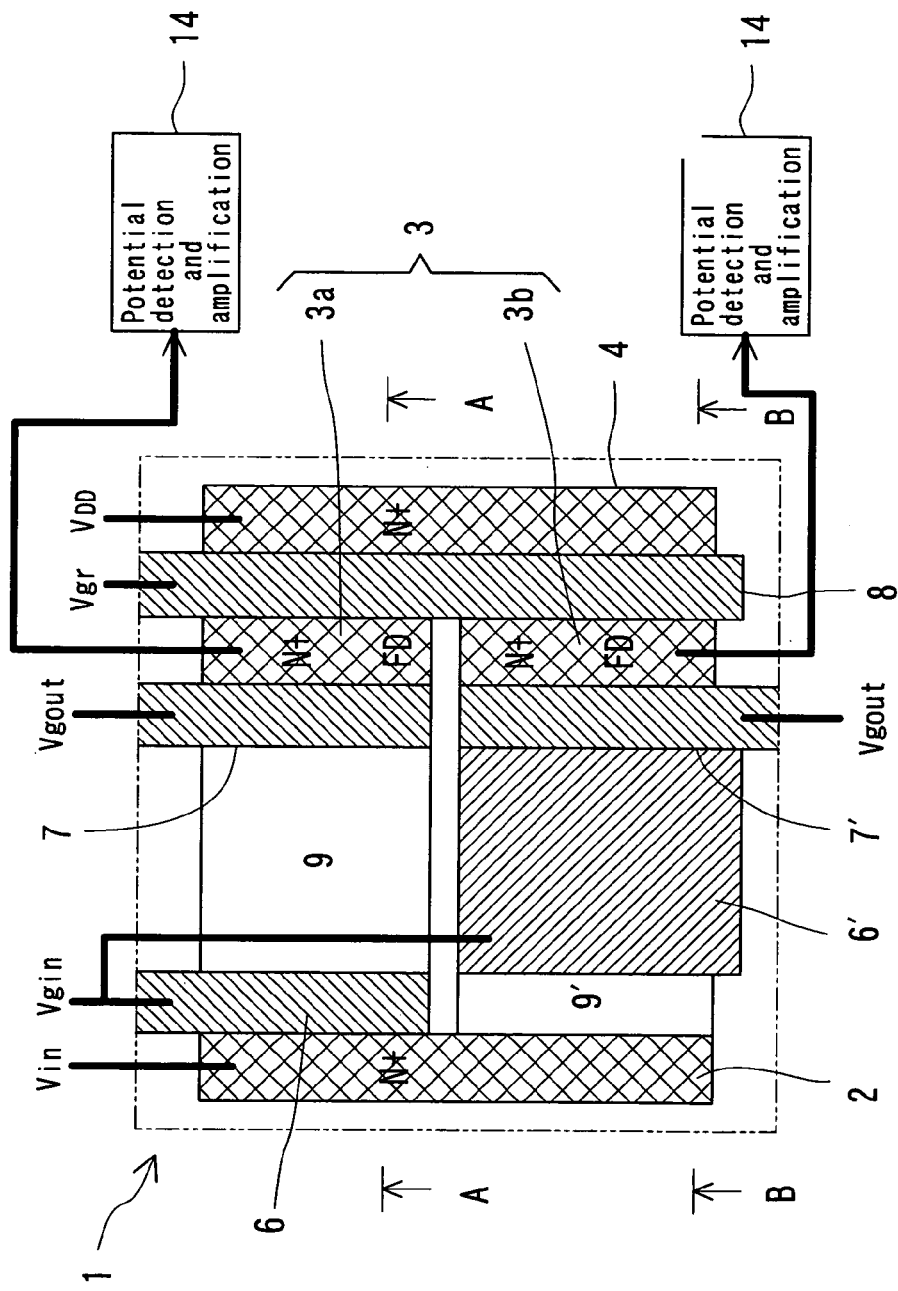
FIG. 6 is a schematic horizontal sectional view showing composite type of FET type sensor in Embodiments 1 and 2 of this invention.

This third type of FET type sensor is an FET type sensor of a wide measuring range covering both plus ion and minus ion, and FIG. 6 shows a horizontal sectional view of essential part of this sensor structure, in which the FET sensors shown in FIG. 1 and FIG. 4 are disposed in a parallel arrangement, and the parts having same functions are identified with same reference numerals.

According to a routine procedure, at the surface side of a substrate 1 of P− type semiconductor, a common input diode 2 and a floating diffusion section 3 comprising a diffusion region reverse to the substrate in conductivity, that is, N+ type are formed across a specific interval, and the floating diffusion section 3 is divided into a first drain 3a (floating diffusion section in first type) and a second drain 3b (floating diffusion section in second type), and the input diode 2 is used as a common source having a portion corresponding to these divided two drains, and first and second mutually parallel channels are formed on the substrate surface between the source and the drains.

At the opposite side to the two channels of the floating diffusion section 3 composing the first and second drains 3a, 3b, a common reset diode 4 comprising an N+ type diffusion region are formed across a small interval from the section 3, and a common reset gate 8 is fixed on a substrate insulation film (not shown) in this interval.

At positions on the substrate insulation film corresponding to both ends of the first channel, an input gate 6 and an output gate 7 of first type are fixed, and at a position on the substrate insulation film corresponding to the middle of the channel (between input and output gates), a sensing section 8 comprising an ion sensitive film is fixed. As a result, the structure of the longitudinal section (for example, section of arrow view A—A in FIG. 6) of the FET type sensor comprising the first channel and reset transistor is same as in FIG. 1A.

At positions on the substrate insulation film corresponding to the middle and terminal end of the second channel, further, an input gate 6' and an output gate 7' of second type are fixed, and at a position on the substrate insulation film corresponding to the initial end of the channel (between the input diode 2 and input gate 6'), a sensing section 9' comprising an ion sensitive film is formed. As a result, the structure of the longitudinal section (for example, section of arrow view B—B in FIG. 6) of the FET type sensor comprising the second channel and reset transistor is same as in FIG. 4A.

In this structure, depending on the depth of the potential well varying with the plus/minus ion density acting on the sensing sections 9 and 9' on the first channel and second channel, and the number of times of seepage of charge from the potential well, the amount of charge accumulated in the first and second drains of the floating diffusion section 3 after potential resetting can be detected as potential change, so that an FET type sensor of wide measuring range is obtained.

As application forms of this composite type sensor, a plurality of the composite type sensor structures are formed on a same semiconductor substrate, thereby compositions of a plurality of complementary nucleic acids in the specimen can be detected simultaneously and efficiently.

As the structural principle obtained from this composite type sensor structure, the sensor structures of the first and second types shown in Embodiments 1 and 2 can be disposed in a plurality of each structure on a same semiconductor substrate, and in this case, at least the input diode, reset gate, and reset diode are used commonly, so that the structure and control can be simplified.

Summing up these Embodiments, this invention realizes the following sensor application structures and measuring methods. A basic form of an application structure is as shown schematically in FIG. 7.

APPLICATION EXAMPLE 1

Figure 7:
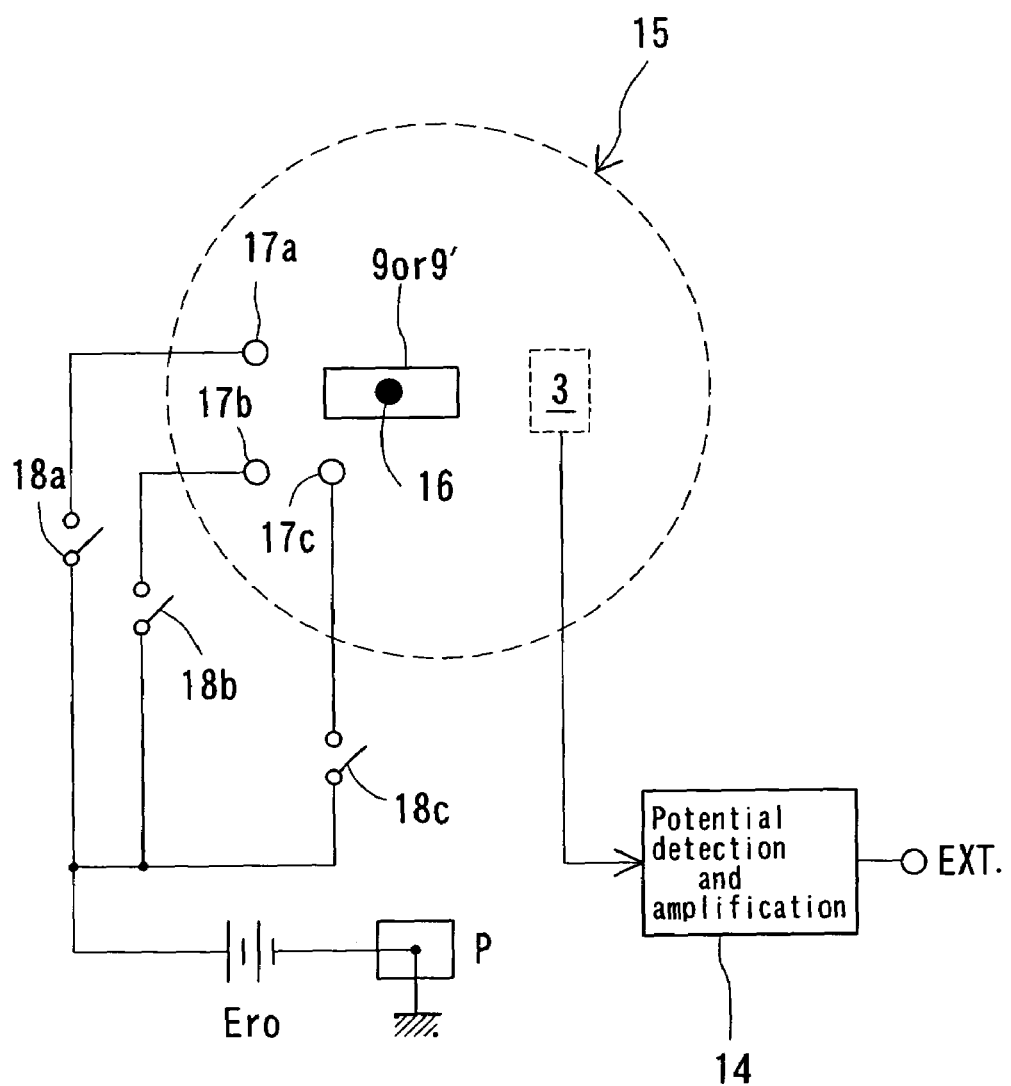
FIG. 7 is a schematic plan view and electric circuit diagram showing a basic structure of application form of FET type sensor of this invention.

In FIG. 7, a broken line circle 15 is a sample solution storing range surrounding the sensing section 9 or 9' comprising an ion sensitive film formed on the surface insulation film of the semiconductor substrate, and the region of the substrate surface (insulation film) including at least its periphery. Those supposed to be included in this range 15, such as gate electrode (concealed beneath the insulation film), diode reverse to the substrate in conductivity type, and other diffusion layer (in this case, N+ layer), are represented by the floating diffusion section 3 relating to the sensor output shown in a broken line frame, and the relation with the sensor entire picture is suggested.

On the sensing section 9 or 9' comprising an ion sensitive film such as Si3N4, a gold film (or a film of material having electrochemical stability and conductivity similar to the properties of gold film; same hereinafter) 16 is formed partly, and near the sensing section 9 or 9' (at the left side and lower left side in the drawing), for example, three gold pads (or pads of material having electrochemical stability and conductivity similar to the properties of gold pads; same hereinafter) 17a, 17b, 17c are fixed, and voltage for measurement or comparison is applied from a battery Ero respectively through switches 18a, 18b, 18c. Other terminal (minus side in this case) of the battery Ero is connected to the reverse side of the substrate p, that is, the grounding potential.

In this structure, a terminal radical of single-strand nucleic acid complementary to a DNA specimen is fixed to the gold film, and the same sample solution is supported in the region including the sensing section (preferably the sensing section 9' corresponding to the conductive channel initial end of the semiconductor) and comparing electrode, and the seepage charge amount from the potential well is measured as cumulative charge of the floating diffusion section 3 on the basis of the potential of the comparing electrode, and hence presence or absence of hybridization of the single-strand nucleic acid and specimen can be detected.

APPLICATION EXAMPLE 2

Figure 8:
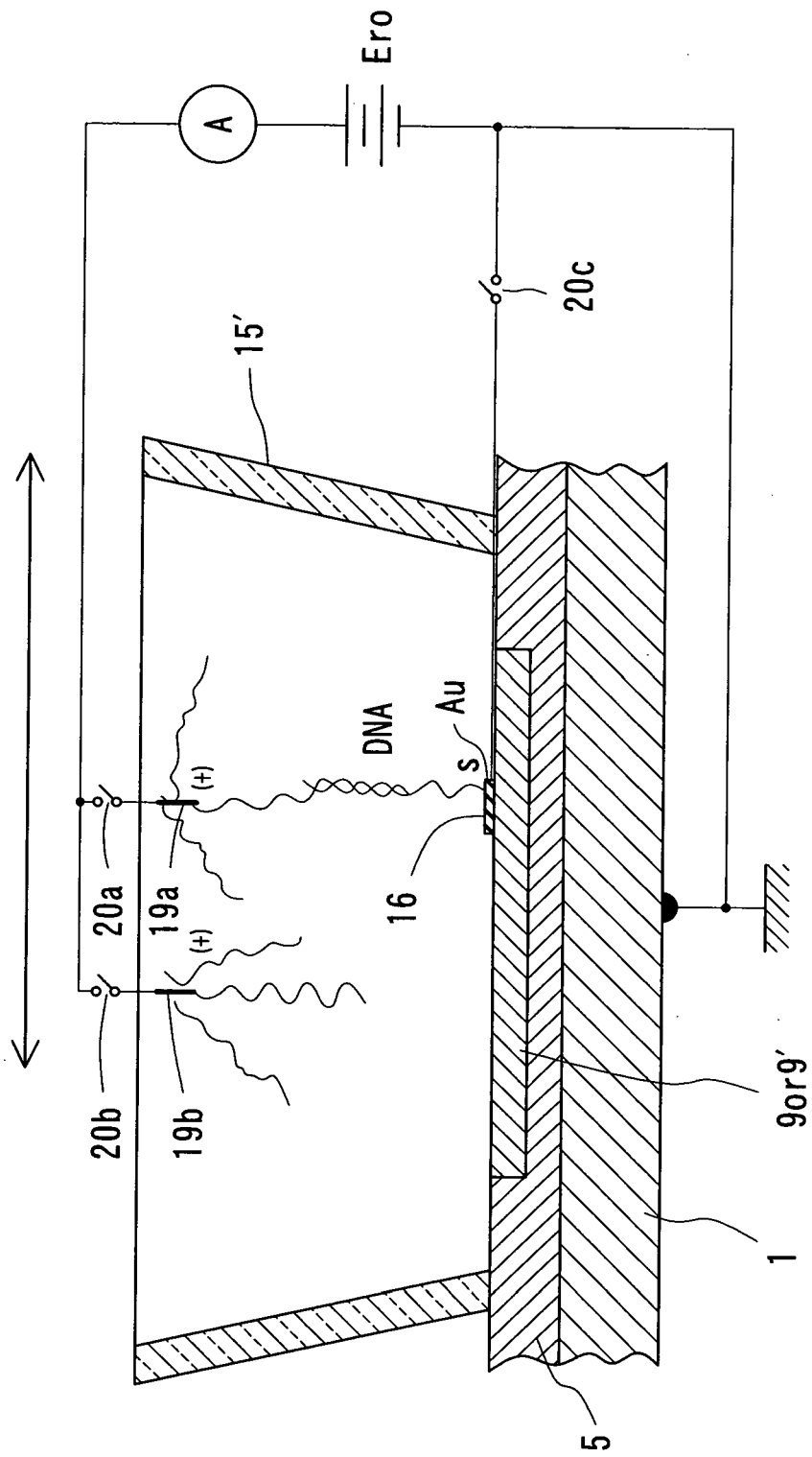
FIG. 8 is a partial sectional view showing an electrode suspension descending system composed as a sensor structure according to an application form.

As a sensor structure of a further application form, the invention composes an electrode suspension descending system as shown in FIG. 8. On an insulation film 5 enclosing a region including at least a sensing section (preferably the conductive channel 9 corresponding to the middle of the conductive channel of semiconductor) on a semiconductor substrate 1, a peripheral wall 15' is erected and formed by an electrochemically inert material such as epoxy glass, and preferably gold measuring electrode 19a and comparing electrode 19b are designed to descend and sink into the sample solution after the measuring electrode 19a is positioned to be right above the gold film 16 in the sensing section 9 or 9'. These electrodes are provided with voltage from battery Ero at the reverse side (grounding potential) of the semiconductor substrate 1 through switches 20a and 20b, or by further closing the switch 20c for directly coupling to the minus side of the Ero from the gold film 16, the flowing current can be measured by an ammeter A.

In this modified structure, a terminal radical (preferably SH radical of cysteine) of single-strand nucleic acid complementary to a DNA specimen is fixed to the gold film 16, and the sample solution is supported by the sensing section by containing in the range of the peripheral wall 15'. In this case, between the measuring electrode 19a and comparing electrode 19b positioned right above the gold film 16, the latter (19b) is supposed to be disposed by deviating a distance not having electric effects on the nucleic acid fixed on the gold film 16.

In the measuring electrode 19a sinking in the sample solution, a proper voltage, for example, 10 mV to 5 V is applied by closing the switch 20a after DNA is hybridized on the nucleic acid fixed on the terminal radical on the gold film. As a result, the free terminal end radical of the hybridized DNA is absorbed on the measuring electrode 19a, and the hybrid DNA is electrically coupled directly, and the voltage by the power source Ero is applied between both ends to energize. Next, the switch 20a is opened and the switch 20b is closed, and the current flowing in the comparing electrode 19b positioned in the solution of the same level as the measuring electrode 19a is measured as reference value.

In this sensor structure, therefore, presence or absence of hybridization can be detected not only by measuring the amount of charge accumulated in the potential well of the FET type sensor, but also by measuring the current flowing in the measuring current as the energizing current of the DNA circuit or the voltage to the grounding potential.

APPLICATION EXAMPLE 3

Figure 9:
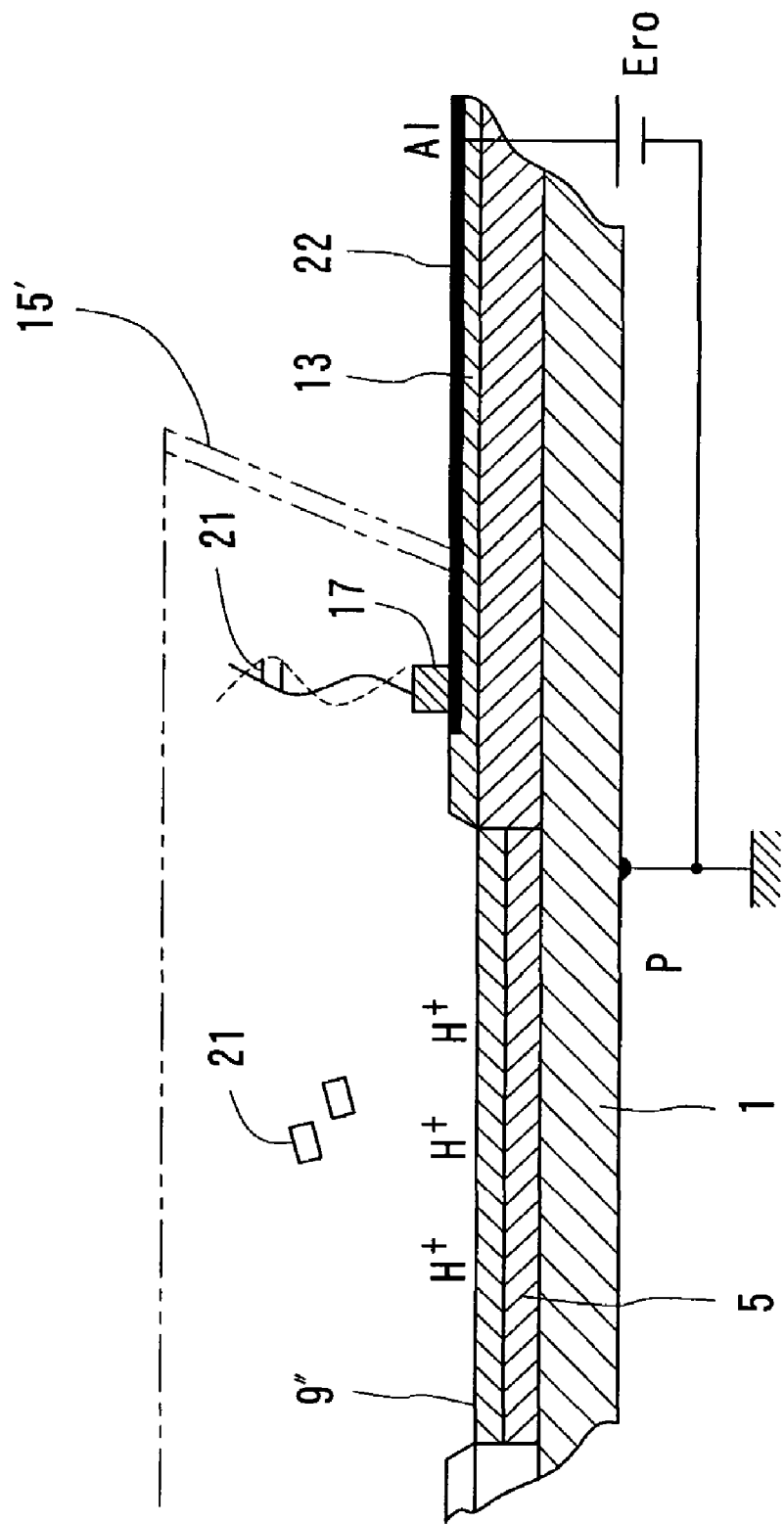
FIG. 9 is a partial sectional view showing a system of using a sensor as PH meter, by using nitride film or tantalum pentoxide film as ion sensitive film, and fixing a terminal end SH radical of single-strand nucleic acid complementary to specimen DNA in at least one of gold pads around the sensing section.

In this example, different from the sensor structure of Application Example 1, as shown in FIG. 9, nitride film or tantalum pentoxide film is used as ion sensitive film of the sensing section 9", and gold pad (not shown) on the film is not used. At least in one of the gold pads (represented by 17) around the sensing section 9", a terminal SH radical of single-strand nucleic acid complementary to the specimen DNA is fixed. A peripheral wall 15' for storing the sample solution and other structure are same as in Application Example 1 (FIG. 7).

In this measuring method, by containing and supporting the sample solution in the region of the peripheral wall 15' including the sensing section 9″ and gold electrode, when there is a specimen DNA complementary to the nucleic acid fixed on a the gold electrode, hybridization takes place. In this state, when there is a hybridiazed DNA, an intercalating agent that can invade between double helices such as product 21 sold as Hoechst 33258 is added to the sample solution.

Then, a positive voltage of power source Ero grounded at the minus side is applied to the gold pad 17 by way of an aluminum lead film 22 on the outer film 13, and the intercalating agent 21 is oxidized because the potential is lowered by the portion of electric resistance of the DNA skeleton conducting with the gold pad 17, so that an oxidizing and reducing current is caused from the intercalating agent 21 to the gold pad 17.

As a result, reaction of 2H+2e=H2 takes place near the DNA, and the PH value (H+ index) of the entire solution phase decreases. In the intercalating agent 21 floating in the aqueous solution, voltage by DNA skeleton is not applied, and it is assumed that oxidation (H+) does not take place substantially. Within the same sensor, or between the adjacent sequential sensors, such DNA fixing gold pads may be disposed in tens to hundreds, and the DNA can be identified by detecting the change of PH when voltage is applied to which gold pad.

Without fixing the DNA terminal radical, the gold pad around the sensing section may be used as comparing electrode. The PH value is the seepage charge amount from the potential well at the depth depending on the PH changes by reference to the potential of the comparing electrode, and the measured value is the index of presence or absence of hybridization of the single-strand nucleic acid and specimen.

Further, the oxidizing and reducing current flowing from the intercalating agent 21 to the gold pad 17 can be also measured by inserting a micro ammeter (not shown) in the voltage application circuit from the power source Ero.

APPLICATION EXAMPLE 4

Figure 10:
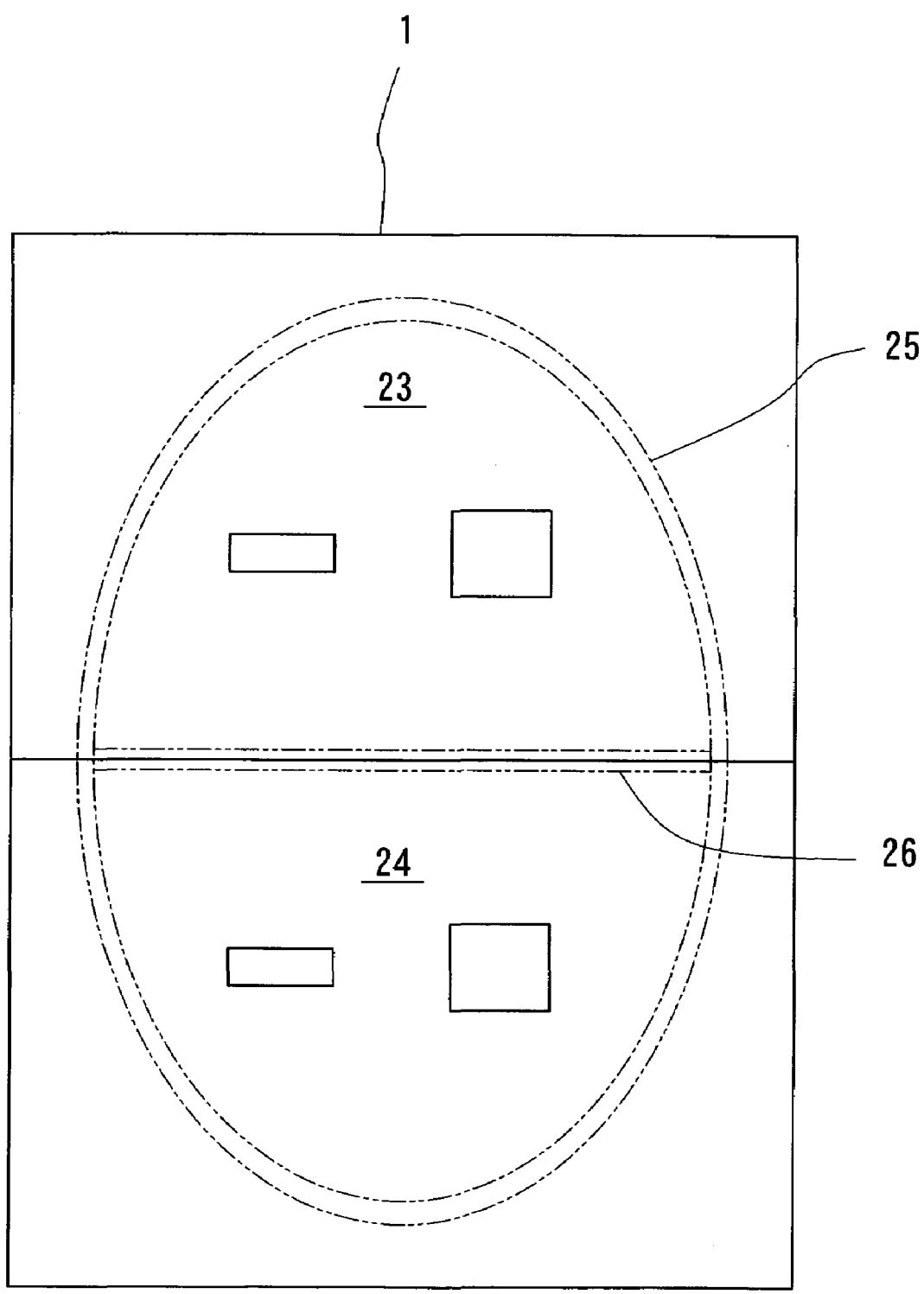
FIG. 10 is a plan view schematically showing a structure in which a pair of FET type sensors are disposed parallel on a same semiconductor substrate 1, an outer peripheral wall of electrochemically inert acrylic glass or the like surrounding the peripheral edge of the pair of FET type sensors in batch are provided together with a partition wall internally contacting with the outer peripheral wall at both ends and partitioning between these sensors.

This invention also presents a sensor structure useful for executing the four method presented herein as shown in FIG. 10, in which a pair of FET type sensors 23, 24 are disposed on a same semiconductor substrate 1, a peripheral wall 25 of electrochemically inert acrylic glass or the like is provided to enclose the peripheral edge of the pair of FET type sensors in batch, and a partition wall 26 having both ends internally contacting with the peripheral wall 25 is provided by partitioning the sensors 23, 24 separately.

As a result, the sample solutions contained in the sensors 23, 24 do not communicate with each other, a target substance reacting with the specimen is fixed on the one sensor only, out of the two adjacent sensors on the same substrate, and nothing is fixed in the other sensor, and by using the same sample solution, the time-course drifts of solution or substance are measured by the other sensor, and the drift value is subtracted from the measured value of the one sensor, so that compatibility of the specimen and target substance can be detected accurately. Of course, different sample solutions can be contained in two sensors, and each can be measured without mutual interference.

INDUSTRIAL APPLICABILITY

As described herein, this invention provides an FET type sensor advanced in sensitivity by comprising a reset transistor and repeating the charge transfer process, in which the sensing section is capable of detecting changes of plus or minus ion density as a result of reaction of sample or specimen, at high sensitivity in a wide range.

Further, by disposing a plurality of FET type sensors of first type and second type, a composite type of the two types, or a plurality of composite types on a same semiconductor substrate, in electrochemical measurement of substance, in particular, in the field of biochemistry, it can be judged whether or not a nucleic acid having a specific base sequence of specific microorganism or disease is contained in the measured sample, and presence or absence of microorganism or disease or content of microorganism can be detected easily and securely, and it also opens up a new direction for measurement of endocrine-disrupting chemicals, dioxins and related substances.

The DNA measuring method of the invention preferably using gold pads or gold electrodes in the FET type sensor is useful for easy, accurate and stable identification of DNA.

What is claimed is:

1. An FET type sensor comprising;
    an input diode section and a floating diffusion section consisting of a diffusion region reverse to the substrate in conductivity type, formed across a specified interval on the face side of a P type or N type semiconductor substrate,
    an input gate and an output gate fixed by way of an insulation film, at positions on the substrate surface corresponding to the initial end and terminal end of a conductive channel formed from the input diode section to the floating diffusion section,
    a sensing section consisting of an ion sensitive film fixed by way of an insulation film, at a position on the substrate surface corresponding to the middle of the channel,
    a reset gate fixed by way of an insulation film, at a position on the substrate surface continuous to the side remote from the channel in the floating diffusion section, and
    a reset diode section consisting of a diffusion region reverse to the substrate in conductivity type, formed on the substrate surface at a side remote from the floating diffusion section in the reset gate,
    wherein a substance reacting or binding with a specimen in the sample in the sensing section or acting as catalyst for reaction of the specimen is fixed in the sensing section, and the electric charge accumulated in the floating diffusion section after resetting of the potential is detected as potential change, depending on the depth of the potential well changed according to the ion density acting on the sensing section and the number of times of seepage from the potential well.

2. The ion sensor of claim 1, wherein the substance to be fixed in said sensing section is a single-strand nucleic acid complementary to the specimen.

3. An FET type sensor comprising;
    an input diode section and a floating diffusion section consisting of a diffusion region reverse to the substrate in conductivity type, formed across a specified interval on the face side of a P type or N type semiconductor substrate,
    an input gate and an output gate fixed by way of an insulation film, at positions on the substrate surface corresponding to the middle and terminal end of a conductive channel formed from the input diode section to the floating diffusion section, a sensing section consisting of an ion sensitive film fixed by way of an insulation film, at a position on the substrate surface corresponding to the input end of the channel, a reset gate fixed by way of an insulation film, at a position on the substrate surface continuous to the side remote from the channel in the floating diffusion section, and a reset diode section consisting of a diffusion region reverse to the substrate in conductivity type, formed on the substrate surface at a side remote from the floating diffusion section in the reset gate, wherein it is designed to detect the electric charge accumulated in the floating diffusion section after resetting of the potential as potential change, depending on the depth of the potential well changed according to the ion density acting on the sensing section and the number of times of seepage from the potential well.

4. The FET type sensor of claim 3, wherein a fixing body reacting or binding with a specimen in sample or catalyzing the reaction of the specimen is fixed in said sensing section.

5. The FET type sensor of claim 4, wherein the substance to be fixed in said sensing section is a single-strand nucleic acid complementary to the specimen.

6. An FET type sensor consisting of a plurality of FET type sensors of claim 3 formed parallel on a same semiconductor substrate, wherein the input gate, reset gate, and reset diode of each sensor element are formed commonly from the single input gate, single reset gate, and single reset diode extending to all elements.

7. An FET type sensor comprising an input diode section and a floating diffusion section consisting of a diffusion region reverse to the substrate in conductivity type, formed across a specified interval on the face side of a P type or N type semiconductor substrate wherein said floating diffusion section is divided into a first drain and a second drain, the input diode section is used as a common source having a portion corresponding to these two divisions, and first and second mutually parallel channels are formed in the substrate surface side between the source and drain, a common reset diode consisting of a diffusion region reverse to the substrate in conductivity type is formed on the side of the floating diffusion section for composing the first and second drains, at the opposite side to the two channels, across a small interval from said floating diffusion section, and a common reset gate is fixed by way of an insulation film on the substrate surface in this small interval, an input gate and an output gate are fixed by way of an insulation film, at positions on the substrate surface corresponding to the both ends of the first channel, and a sensing section consisting of an ion sensitive film is fixed by way of an insulation film, at a position on the substrate surface corresponding to the middle of the first channel, an input gate and an output gate are fixed by way of an insulation film, at positions on the substrate surface corresponding to the middle and terminal end of the second channel, and a sensing section consisting of an ion sensitive film is fixed by way of an insulation film, at a position on the substrate surface corresponding to the initial end of the second channel, and it is designed to detect the electric charge accumulated in the first and second drains of the floating diffusion section after resetting of the potential as potential change, depending on the depth of the potential well changed according to the ion density acting on each sensing section on the first channel and second channel and the number of times of seepage from the potential well.

8. A parallel FET type sensor forming a plurality of FET type sensors of claim 7 on a same semiconductor substrate.

* * * * *

UNITED STATES PATENT AND TRADEMARK OFFICE
CERTIFICATE OF CORRECTION

PATENT NO. : 7,049,645 B2
APPLICATION NO. : 10/495808
DATED : May 23, 2006
INVENTOR(S) : Sawada et al.

It is certified that error appears in the above-identified patent and that said Letters Patent is hereby corrected as shown below:

Title page, item (73), the assignee should read:
--Bio-X Inc., Kyoto (JP); Kazuaki Sawada, Aichi (JP)--.

Signed and Sealed this

Fifth Day of September, 2006

JON W. DUDAS
*Director of the United States Patent and Trademark Office*